United States Patent [19]
Ellison

[11] Patent Number: 5,260,498
[45] Date of Patent: Nov. 9, 1993

[54] DIELS-ALDER PROCESS

[75] Inventor: Robert H. Ellison, Houston, Tex.

[73] Assignee: Shell Oil Company, Houston, Tex.

[21] Appl. No.: 987,096

[22] Filed: Dec. 7, 1992

Related U.S. Application Data

[63] Continuation of Ser. No. 819,037, Jan. 10, 1992, abandoned.

[51] Int. Cl.$^5$ .............................................. C07C 2/50
[52] U.S. Cl. ...................... 585/361; 526/75; 526/133; 526/166; 526/281; 526/282; 526/308; 585/502
[58] Field of Search ................ 585/502, 361; 526/75, 526/133, 166, 281, 282, 308

[56] References Cited

U.S. PATENT DOCUMENTS

| 4,891,460 | 1/1990 | Ishii | 585/361 |
|---|---|---|---|
| 5,068,296 | 11/1991 | Hara et al. | 585/361 |
| 5,095,082 | 3/1992 | Kelsey | 585/361 |
| 5,143,992 | 9/1992 | Kelsey | 585/361 |
| 5,196,621 | 3/1993 | Diesen et al. | 585/530 |

FOREIGN PATENT DOCUMENTS

| 1227894 | 11/1966 | Fed. Rep. of Germany. |
| 63-92640 | 4/1988 | Japan. |
| 92/22597 | 12/1992 | World Int. Prop. O. |

OTHER PUBLICATIONS

Chemical Abstracts, vol. 82, No. 25, issued Jun. 23, 1975 (Columbus, Ohio, USA), T. Akima et al. "5-(3'-cyclohexenyl)norbornene", p. 477, col. 1, Abstract No. 170 222j Japan 74 26,619 (Hitachi Chemical).
CA:82 170222j, T. Akima and H. Kawauchi [Hitachi Chemical Co., Ltd.], JP49026619 (Jul. 10, 1974), Appl. JP70105816 (Dec. 2, 1970).
CA:77 88129x, S. Tsuchida, et al, "Diels-Alder reaction between butadiene and cyclopentadien. Reaction of cyclopentaidene with the products," *Sekiyu Gakkai Shi,* 15, 294 (1972).
CA:66 28447n, W. Mack and H. Anselm [Consortium fuer Elektrochemische Industrie G.m.b.H], DE 1227894 (Nov. 3, 1966).
CA:64 6510e, G. Sartori, et al, "Synthesis of alkenyl norbornenes," *Chim. Ind.* (Milan), 47, 1331 (1965).
CA:77 164108g, S. Tsuchida, et al, (Fac. Eng., Kansai Univ., Osaka, Japan), "Synthesis of unconjugated cyclodienes by the Diels-Alder reaction. VI.," *Sekiyu Gakkai Shi* 1972, 15(8) (Japan).
CA:77 19249z, S. Tsuchida, et al, (Fac. Eng., Kansai Univ. Suita, Japan), "Diels-Alder reaction between butadiene and cyclopentadiene. Determination of trimers." *Sekiyu Gakkai Shi* 1972 15(3), 189-92 (Japan).
CA:77 19250t, S. Tsuchida, et al, "Diels-Alder reaction between butadiene and cyclopentadiene. Trimers in reaction products." *Sekiyu Gakkai Shi* 1972, 15(3) 193-6 (Japan).
CA:82 170221h, M. Ogawa, et al, (Mitsubishi Petrochemical Co., Ltd.), "Vinylnorbornene" Japan 74 25,665 (Cl. C 07cb) Jul. 2, 1974 Appl. 70 20,817 Mar. 13, 1970.
S. R. Wallis, "4-Vinyltricyclo[6.2.1.$^{2,7}$]undec-9-ene. Minor adduct from the Diels-Alder reaction of 4-vinylcyclohexene and cyclopentadiene," *J. Chem. Soc. Perkin Trans.* 1, 1647 (1972).

*Primary Examiner*—Anthony McFarlane

[57] ABSTRACT

An improved process for the production of 1:1 molar adducts of 4-vinylcyclohexene and cyclopentadiene, primarily 5-(3-cyclohexen-1-yl)-2-norbornene, comprises contacting 4-vinylcyclohexene and dicyclopentadiene at elevated temperature in a suitable reactor, separating the resulting mixture of adducts into light product comprising predominately the 1:1 molar adduct and a heavy product comprising higher adducts and cyclopentadiene oligomers, and recycling the bottoms product to the reactor.

10 Claims, No Drawings

DIELS-ALDER PROCESS

This is a continuation of application Ser. No. 819,037, filed Jan. 10, 1992, now abandoned.

FIELD OF THE INVENTION

This invention relates to an improved process for the production of a Diels-Alder adduct of 4-vinylcyclohexene and cyclopentadiene. More particularly, the invention relates to an improved process for the production of 5-(3-cyclohexen-1-yl)-2-norbornene.

BACKGROUND OF THE INVENTION

The ring-opening or metathesis polymerization of a wide variety of cyclic and polycyclic olefins is well known. Numerous patents and literature references, both U.S. and foreign, relate to the ring opening polymerization of olefins such as dicyclopentadiene in the presence of olefin metathesis catalyst systems. An illustrative catalyst system is disclosed by Sjardijn et al, U.S. Pat. No. 4,810,752, wherein substituted phenolic tungsten halides are employed in conjunction with triorganotin hydrides.

It is characteristic of many if not most ring-opening polymerizations that all carbon-carbon double bonds present in the ring or rings of the monomeric reactants are involved in the ring-opening polymerization. Thus, when one or more of the monomeric reactants contains multiple carbon-carbon double bonds the resulting polymer is a highly crosslinked thermoset polymer. These thermoset polymers exhibit a variety of useful properties but the nature of such properties is somewhat limited by the highly crosslinked character of the polymer.

In copending U.S. patent application Ser. No. 733,579 (T-2399), filed Jul. 22, 1991, there is described the preparation of Diels-Alder adducts of 4-vinylcyclohexene and cyclopentadiene. Among these adducts is a monoadduct, i.e., 5-(3-cyclohexen-1-yl)2-norbornene. The ring-opening polymerization of this adduct is particularly useful because the polymer exhibits a varying degree of crosslinking, depending in part upon the polymerization environment. The resulting polymer, when not highly crosslinked, is useful in applications not available to thermoset polymers.

The 5-(3-cyclohexen-1-yl)-2-norbornene adduct, a 1:1 adduct of 4-vinylcyclohexane and cyclopentadiene, is produced together with other products by conventional Diels-Alder technology. However, the process selectivity to this particular adduct is lower than desired, e.g., 60% to 65%. The other reaction products include higher adducts of 4-vinylcyclohexene and cyclopentadiene, i.e., adducts with a higher proportion of cyclopentadiene, and cyclopentadiene oligomers. It would be of advantage to provide an improved process to increase the overall selectivity of the Diels-Alder process to the desired mono-adduct and decrease the overall production of heavier products.

SUMMARY OF THE INVENTION

The present invention provides an improved process for the production of Diels-Alder mono-adducts of 4-vinyl-cyclohexene and cyclopentadiene. More particularly, the invention provides such an improved process wherein the overall selectivity to desired mono-adduct is increased and the overall production of heavier by-products is decreased.

DESCRIPTION OF THE INVENTION

The process of the invention comprises a process in which 4-vinylcyclohexene and dicyclopentadiene are contacted at elevated temperature under Diels-Alder reaction conditions to produce an initial product mixture containing 5-(3-cyclohexen-1-yl)-2-norbornene, a mono-adduct, and heavier products including higher adducts of 4-vinylcyclohexene and cyclopentadiene and cyclopentadiene oligomers. This initial product mixture is separated into a mono-adduct portion and a heavier product portion and the heavier products are recycled to the Diels-Alder reactor where contact with additional 4-vinylcyclohexene produces additional monoadduct.

The desired products of the Diels-Alder process of the invention are mono-adducts, i.e., 1:1 molar adducts, of 4-vinylcyclohexene and cyclopentadiene. When 4-vinylcyclohexene and cyclopentadiene, usually provided as dicyclopentadiene, are heated at an elevated temperature, a variety of adducts are produced including 1:1 molar adducts, 1:2 molar adducts of 4-vinylcyclohexene and cyclopentadiene, 1:3 molar adducts of 4-vinylcyclohexene and cyclopentadiene, higher molar adducts of 4-vinylcyclohexene and cyclopentadiene, and a number of cyclopentadiene Diels-Alder oligomers such as trimers, tetramers, pentamers and higher adducts. Of the 1:1 molar adducts, two adducts are stereoisomers of 5-(3-cyclohexen-1-yl)-2-norbornene, represented by the following formulas,

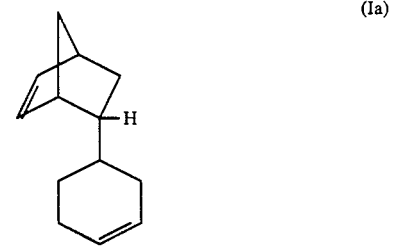

(Ia)

(Ib)

and a third type of 1:1 molar adduct is represented by the formula

(II)

The isomers represented by the formulas Ia and Ib are isomers of 5-(3-cyclohexen-1-yl)bicyclo[2.2.1]hept-2-ene or, in more common terms, 5-(3-cyclohexen-1-yl)-2-norbornene. The isomer Ia is termed an "endo" isomer and the isomer Ib is termed an "exo" isomer as reflects the steric relationship of the cyclohexene substituent to the non-planear 6-membered ring of the norbornene moiety. As stated, the process of producing the above Ia, Ib and II adducts also produces other adducts and cyclopentadiene oligomers.

The 4-vinylcyclohexene precursor of the adducts is a well known compound illustratively produced by thermal dimerization of butadiene. The dicyclopentadiene source of cyclopentadiene is also well known and is often obtained as a by-product of olefin crackers. Dicyclopentadiene also exists in endo and exo stereoisomeric forms. Either stereo-isomer, or a mixture of both isomers, is suitably employed to produce the vinylcyclohexene/cyclopentadiene adduct mixture of the invention. Particularly useful are commercially available technical grades of dicyclopentadiene having a purity from about 85% to about 95%. These technical grades are easily processed by virtue of being liquid at ambient temperature whereas the pure endo-dicyclopentadiene is normally a solid melting at 32° C.

The Diels-Alder formation of vinylcyclohexene/cyclopentadiene adducts is conducted in a suitable reactor at an elevated temperature and a convenient pressure which is typically greater than ambient pressure. Suitable temperatures are usually above about 160° C. and temperatures from about 180° C. to about 260° C. are preferred. Because of the reactive nature of the monomeric olefins and/or the adduct products it is desirable that the reaction be conducted in an inert reaction environment and traces of reactive materials such as oxygen should be excluded. The inclusion of free radical scavengers is also useful on occasion. Although the use of a reaction diluent is not precluded in the adduct formation process, the preferred production of Diels-Alder adducts is conducted in the substantial absence of reaction diluents. The reaction of 4-vinylcyclohexene and dicyclopentadiene under the above conditions produces the above 1:1 molar adducts as well as cyclopentadiene oligomers and higher adducts having greater proportions of cyclopentadiene.

To obtain the mono-adduct product in a purity useful in ring-opening metathesis polymerization, the mixture of unreacted 4-vinylcyclohexene, adducts and cyclopentadiene oligomers is separated to provide a fraction at least substantially enriched in the 5-(3-cyclohexen-1-yl)-2-norbornene isomers (isomers Ia and Ib). The separation is effected by conventional physical methods. In a preferred modification the separation is effected by fractional distillation, generally at a substantially reduced pressure. An initial preliminary separation is conveniently made with the use of a simple distillation column or a wiped film evaporator. More effective separation results from a distillation in a multi-tray distillation column. Careful separation by distillation typically results in 1:1 adduct mixtures as light or overhead product having as much as 90% by weight and preferably as much as 95% by weight of a mixture of isomers Ia and Ib with a lesser amount of the isomer II and small amounts of unreacted starting monomer, higher adducts and cyclopentadiene oligomers. The heavy or bottoms product of a separation by distillation is a mixture consisting primarily of higher adducts and cyclopentadiene oligomers.

The selectivity to the mono-adduct mixture is good, typically on the order of about 60% to about 65%, based on limiting reactant which is generally cyclopentadiene. The heavy product, about 35% to about 40% of the product mixture is heavier material and is not directly useful in the production of olefin metathesis product of a variable extent of crosslinking. This heavy material has value as fuel, or is disposed of by conventional hydrocarbon disposal methods. In the process of the invention, however, the heavy product from the mono-adduct separation is recycled to a Diels-Alder reactor to which 4-vinylcyclohexene is added and in which additional adducts of 4-vinylcyclohexene and cyclopentadiene, including the mono-adduct, are formed. It is useful to employ one or more separate reactors wherein the bottoms product contacts fresh 4-vinylcyclohexene to form a Diels-Alder adduct mixture including mono-adduct. The conditions of such contacting are the same as or similar to those under which the initial adduct formation took place. Those conditions include a temperature of above about 160° C. and preferably from about 180° C. to about 260° C. The pressure is greater than ambient pressure, typically from about 100 psig to about 200 psig. In a preferred embodiment, however, a single Diels-Alder reactor system is employed wherein the bottoms product from the mono-adduct separation is recycled to the reactor to which 4-vinylcyclohexene and any necessary dicyclopentadiene are added. Thus, a continuous process is made possible wherein bottoms product, subsequent to separation of mono-adduct from a Diels-Alder adduct mixture as by distillation, is recycled to the Diels-Alder reactor to in effect provide cyclopentadiene for subsequent production of additional mono-adduct. The desired 1:1 adduct is primarily found in the overhead product which is useful as such in metathesis polymerization or is further separated by conventional techniques to afford purer 1:1 adduct. The process of the invention, from an overall standpoint, increases the overall conversion of starting monomer and reduces the production of heavier materials as the conversion of recycled bottoms product to mono-adduct is on the order of about 50% per pass. Thus, the production of mono-adduct is enhanced and the problems of use or disposal of the heavier materials are reduced. The enhanced overall conversion to the desired mono-adduct results in better economics for the production of desired mono-adduct and the reduction of ecological problems resulting from the need to burn or otherwise dispose of the heavier products is reduced.

The mono-adduct product of the process of the invention, primarily 5-(3-cyclohexen-1-yl)-2-norbornene isomers, is polymerized by conventional olefin metathesis processes employing conventional olefin metathesis catalyst systems. Also illustrative of this polymerization is copending U.S. Ser. No. 733,579, filed Jul. 22, 1991. When a relatively impure mono-adduct mixture, e.g., a mixture containing some proportion of heavier cyclopentadiene oligomers or crosslinking agents, is polymerized, a crosslinked thermoset polymer is obtained which has many of the properties of other thermoset polymers but additionally exhibits an elasticity which most thermoset polymers do not have. Such thermoset polymers find utility in electric and electronic applications, e.g., circuit boards and encapsulating material. When a relatively pure mono-adduct mixture is polymerized in the absence of crosslinking agents, the polymer evidences little or no crosslinking and is thermoplastic in character. Such polymers show toughness and strength as well as elasticity and are processed by methods conventional for thermoplastic polymers, e.g., extrusion or injection molding. Specific application is in the production of parts and housings for automotive applications.

The invention is further illustrated by the following Illustrative Embodiments which should not be regarded as limiting.

ILLUSTRATIVE EMBODIMENT I

Dicyclopentadiene and 4-vinylcyclohexene in equimolar mixture were heated in an autoclave at 240° C. for 4 to 4.5 hours. The reaction product was diluted with cyclohexane and passed through a packed bed of alumina in order to remove the t-butylcatechol inhibitor introduced with the monomeric reactants. The resulting mixture was distilled in a wiped film evaporator at 3 mm Hg pressure at 90° C. to afford a light fraction containing unreacted vinylcyclohexene and dicyclopentadiene and the mono-adducts of 4-vinylcyclohexene and cyclopentadiene. A 150 ml sample of this distillate was vacuum distilled using a 10-tray Oldershaw column to give 4 fractions. The fourth fraction, 65 g, was shown by gas chromatographic analysis to consist of 0.15% dicyclopentadiene, 88.3% endo-5-(3-cyclohexen-1-yl)-2-norbornene, 6.1% exo-5-(3-cyclohexen-1-yl)-2-norbornene and two additional components present in the amounts of 1.9% by mole and 2.4% by mole, respectively, which are believed to be isomeric adducts of the above formula II, several additional components totalling about 0.4% mole, 0.4% mole of tricyclopentadiene and about 0.4% mole unidentified products. Analysis of this fraction by nuclear magnetic resonance indicated about 87% mole of the above endo product, about 9% mole of the above exo adduct and about 5% mole of isomeric adducts of the above formula II.

ILLUSTRATIVE EMBODIMENT II

A sample of primarily 1:2 molar adduct of 4-vinylcyclohexene (VCH) and cyclopentadiene (CPD) was obtained by separation of the reaction product of VCH and dicyclopentadiene (DCPD). The predominately 1:2 molar adduct was taken as illustrative of the heavier product obtainable upon separation of the above reaction product. The 1:2 adduct was contacted with VCH in an autoclave of 300 ml capacity at 240° C. for 2 hours. Samples were removed at intervals from the resulting mixture and analyzed by capillary gas chromatography. The composition of the resulting mixtures was determined by measuring the areas under the gas chromatography curves according to standard techniques. These compositions are shown in Table I.

TABLE I

| Reaction Time. hrs | 0 | 1 | 2 |
|---|---|---|---|
| Composition, % | | | |
| VCH | 54.6 | 43.9 | 45.0 |
| DCPD | 2.5 | 0.5 | 0.4 |
| 1:1 adduct | 5.0 | 25.1 | 28.5 |
| CPD trimer | 1.4 | 1.5 | 1.2 |
| 1:2 adduct | 34.8 | 22.2 | 17.3 |
| CPD tetramer | 0.2 | 0.9 | 1.1 |
| 1:3 adduct | 0.0 | 4.0 | 3.5 |
| CPD pentamer | 0.0 | 0.5 | 1.3 |

Illustrative Embodiment III

The procedure of Illustrative II was repeated except that the entire bottoms product resulting from removal by distillation of the 1:1 molar adduct of VCH and DCPD from an adduct mixture produced by a process similar to Illustrative Embodiment I was contacted with VCH and the mixture was maintained in the 300 ml autoclave for 4 hours. The composition of the resulting mixtures, measured at intervals, is shown in Table II.

TABLE II

| Reaction Time. hrs | 0 | 0.5 | 1.5 | 4 |
|---|---|---|---|---|
| Composition, % | | | | |
| VCH | 78.5 | 74.2 | 68.7 | 66.5 |
| DCPD | 0.0 | 0.0 | 0.0 | 0.0 |
| 1:1 adduct | 0.2 | 7.9 | 16.7 | 20.6 |
| CPD trimer | 2.7 | 2.3 | 1.8 | 1.3 |
| 1:2 adduct | 14.1 | 10.2 | 7.2 | 6.0 |
| CPD tetramer | 0.8 | 0.9 | 1.0 | 1.1 |
| 1:3 adduct | 2.0 | 1.8 | 1.6 | 1.3 |
| CPD pentamer | 0.7 | 1.0 | 1.2 | 1.2 |

What is claimed is:

1. In a process for producing 1:1 molar adduct of 4-vinylcyclohexene and cyclopentadiene by reacting 4-vinylcyclohexene and dicyclopentadiene to form a product mixture, the improvement which comprises:
   (a) separating said product mixture comprising 1:1 molar adduct of 4-vinylcyclohexene and cyclopentadiene, higher adducts of 4-vinylcyclohexene and cyclopentadiene and cyclopentadiene oligomers into a light product comprising primarily said 1:1 molar adduct and a heavy product comprising said higher adducts and cyclopentadiene oligomers;
   (b) passing at least a portion of the heavy product to a reactor wherein the heavy product contacts additional 4-vinylcyclohexene at a temperature of above about 160° C. to produce 1:1 molar adduct of 4-vinylcyclohexene and cyclopentadiene; and
   (c) recovering said 1:1 molar adduct.

2. The process of claim 1 wherein the separation of light product from heavy product is by distillation.

3. The process of claim 2 wherein the heavy product is contacted with additional 4-vinylcyclohexene at a pressure of greater than ambient pressure.

4. The process of claim 3 wherein the heavy product and the 4-vinylcyclohexene are contacted at a temperature within the range from about 180° C. to about 260° C.

5. A process for producing 1:1 molar adduct of 4-vinylcyclohexene and cyclopentadiene comprising the steps of:
   (a) contacting 4-vinylcyclohexene and dicyclopentadiene in a first reactor under conditions effective to produce 1:1 molar adduct of 4-vinylcyclohexene and cyclopentadiene thereby producing a product mixture comprising 1:1 molar adduct of 4-vinylcyclohexene and cyclopentadiene, higher adducts of 4-vinylcyclohexene and cyclopentadiene and cyclopentadiene oligomers;
   (b) separating the resulting product mixture into a light product comprising primarily said 1:1 molar adduct and a heavy product comprising said higher adducts and cyclopentadiene oligomers,
   (c) passing at least a portion of the heavy product to a second reactor wherein the heavy product contacts additional 4-vinylcyclohexene at a temperature of above about 160° C. to produce 1:1 molar adduct of 4-vinylcyclohexene and cyclopentadiene; and
   (d) recovering said 1:1 molar adduct.

6. The process of claim 5 wherein the separation of light product from heavy product is by distillation.

7. The process of claim 6 wherein the heavy product and additional 4-vinylcyclohexene are contacted at a temperature within the range from about 180° C. to about 260° C.

8. A process for producing 1:1 molar adduct of 4-vinylcyclohexene and cyclopentadiene comprising the steps of:

(a) contacting 4-vinylcyclohexene and dicyclopentadiene in a reactor at a temperature of above about 160° C. to produce a product mixture comprising 1:1 molar adduct of 4-vinylcyclohexene and cyclopentadiene, higher adducts of 4-vinylcyclohexene and cyclopentadiene and cyclopentadiene oligomers;

(b) separating the resulting product mixture into a light product comprising primarily said 1:1 molar adduct and a heavy product comprising said higher adducts and cyclopentadiene oligomers, (c) passing at least a portion of the heavy product to the reactor in step (a) wherein the heavy product contacts additional 4-vinylcyclohexene at a temperature of above about 160° C. to produce 1:1 molar adduct of 4-vinylcyclohexene and cyclopentadiene; and (d) recovering said 1:1 molar adduct.

9. The process of claim 8 wherein the separation of light product from heavy product is by distillation.

10. The process of claim 9 wherein the heavy product and 4-vinylcyclohexene are contacted at a temperature within the range from about 180° C. to about 260° C.

* * * * *